United States Patent [19]
Iizuka et al.

[11] 3,961,938
[45] June 8, 1976

[54] SUBSTANCE USEFUL FOR GROWTH OF PLANTS AND PROCESS FOR MANUFACTURING THE SAME

[76] Inventors: Chiyokichi Iizuka, 121 Shimizu, Noda, Chiba; Chohachi Fumoto, 2-7-46, Kawarasone, Koshigaya, Saitama, both of Japan

[22] Filed: Nov. 8, 1974

[21] Appl. No.: 522,249

[30] Foreign Application Priority Data
Aug. 2, 1974  Japan.............................. 49-88767

[52] U.S. Cl............................... 71/97; 260/209 R; 260/236.5; 260/429 R; 424/195; 47/1.1; 71/77
[51] Int. Cl.²............................................ A01N 9/00
[58] Field of Search ...................... 71/97, 79; 47/1.1

[56] References Cited
UNITED STATES PATENTS

| | | | |
|---|---|---|---|
| 1,833,089 | 11/1931 | Morimoto............................. | 47/1.1 |
| 2,005,365 | 6/1935 | Giacinto.................................. | 47/1.1 |
| 2,262,851 | 11/1941 | Lescarboura........................... | 47/1.1 |
| 2,723,493 | 11/1955 | Stoller.................................... | 47/1.1 |
| 3,361,555 | 1/1968 | Herschler............................... | 71/77 |

FOREIGN PATENTS OR APPLICATIONS

| | | | |
|---|---|---|---|
| 46-28125 | 8/1971 | Japan..................................... | 71/97 |
| 40-21213 | 9/1965 | Japan..................................... | 71/79 |

OTHER PUBLICATIONS

Iizuka et al., "Extraction of Medicinal Subs. From Edible, etc.;" (1973) CA 79 No. 9879g, (1973).

*Primary Examiner*—Glennon H. Hollrah
*Attorney, Agent, or Firm* — Haseltine, Lake & Waters

[57]  ABSTRACT

A substance useful for the growth of plants, which is produced from the hyphae of an edible fungus such as shiitake and contains organic germanium as main effective ingredient, as well as a process of manufacturing the same.

9 Claims, No Drawings ically, it is a semiconductor and finds extensive applications in the electronic field, particularly for amplification and modulation purposes, as is well known in the art.
SUBSTANCE USEFUL FOR GROWTH OF PLANTS AND PROCESS FOR MANUFACTURING THE SAME

BACKGROUND OF THE INVENTION

This invention relates to substances useful for accelerating or promoting the growth of plants, which substances are derived from the hyphae of edible fungi such as shiitake and whose main effective ingredient is germanium present in the form of organic compounds, and also to the manufacture of the same.

Germanium, the atomic number of which is 32, occurs in nature in the form of certain compounds in various parts of the earth. It has a bright grey color, is hard and brittle and has a metal-like appearance. Actually, it is a semiconductor and finds extensive applications in the electronic field, particularly for amplification and modulation purposes, as is well known in the art.

In the mean time, germanium is known to be contained in coal, and hence in vegetation. Also, it is found that germanium is contained in great quantities in any of bamboo grasses, new shoots of tea and leaves of oak (as reported in Asai Germanium Research Institute Report Vol. 1, issued in December, 1971). Further, some plants valuable in medicine have the following germanium contents (as stated in the same report).

|  |  |
|---|---|
| Aloe | 77 ppm |
| Comfrey | 152 ppm |
| Chlorella | 76 ppm |
| Garlic | 754 ppm |
| Bandai udo | 72 ppm |
| Bandai mushroom | 255 ppm |

By the way, it is said that in Korea there are few people suffering from cancer. This is thought to have a close bearing upon the fact that garlic is a daily food there, the aforementioned surprising germanium content in the garlic perhaps playing an important role in keeping cancer in check.

The aforesaid report further gives results of research concerning the relation between germanium and growth of plants. It says that marked differences are noted in the growth and flavor between ginseng sprayed with a dilute water solution of some complex salt of germanium and an unsprayed one, and that germanium is a must for the growth of plants. Regarding the causes for these differences, the report explains that the ginseng is perhaps very susceptible to numerous viruses and bacteria present in the soil and readily attacked by these enemies under the usual circumstances, but by taking in germanium it will produce a powerful arm (probably some biocatalysts or enzymes) which is well able to cope with and destroy the enemies.

Despite the fact that germanium is very important for the growth of plants, the conventional method of cultivation has had an inherent problem that the yield of the seed or fruit crop has been unsatisfactory in spite of the flourishing growth of stalks and leaves.

As a typical example, the yield of soybeans is very low in Japan. This is due, at least partly, to the fact that the productivity of this crop plant there is too low to let this crop stand in the international competition and that unlike rice and sugar beet no government help has heretofore been given to this crop. After all, the yield of this crop, unlike rice, has not been substantially improved for the last several decades. In fact, the average yield of the soybean is 11 to 14 kilograms per acre and has not been practically increased since about 1930. On the other hand, the yield of rice, which was below 30 kilograms per acre in the 1930's, is now about to exceed 50 kilograms per acre. Among the factors for the obstructed improvement of the yield of the soybean is the fact that this crop plant is poorly sensitive to manuring. The poor sensitivity of a plant to manuring means its tendency to permit little increase of the yield by increasing the manure. In Hokkaido, it is customary to give only 0.05 to 0.2 kilograms per acre of nitrogen as manure. This quantity is required to ensure the growth in the initial stage. However, the supply of further nitrogen is not thought to be needed for fixed nitrogen is taken in from the root; rather, it is thought to be wasteful since it merely promotes the growth of stalks and leaves. For this reason, few attempts to increase the yield by improving the way of supplying nitrogen have been reported. Similarly, no pronounced increase of yield is obtainable by increasing the amounts of phosphoric acid and potassium supplied, and hence there are few reports on relevant experiments and research. ("Soybeans Culture Technical Data," No. 3, 1974, issued by General Department, Shizai Engei Headquarters, Zenno).

Before the instant invention, the inventors had been studying the hyphae of edible fungi for many years. Particularly, they were interested in the metabolic products and liquids in the cells of these hyphae and made extensive experiments concerning the utility and method of extraction of these substances. As a result, they found that liquid extracts produced through self-digestion of the hyphae with enzymes resulting from the metabolic process in the hyphal body, i.e., $\beta$-1-3 glucanase and chitinase, had the effects of reducing blood pressure and holding cancer in check and also served as an effective herbicide for moss.

The inventors endeavored in further investigations and researches to expand the above findings, and they casually obtained markedly better growth of soybean, eggplant, tomato and other crop plants by spraying the leaves of these plants with a dilute solution of a liquid extract derived from the hyphae of shiitake. Particularly, the yield of the soybean could be surprisingly increased. Theoretically, it was impossible to attribute this result to the effect of the sole self-digestion liquids resulting from self-digestion with $\beta$-1-3 glucanase and chitinase. In an effort to clarify the causes, it was assumed that germanium, which was known to be taken in many plants, had something to do with the facts that the liquid extract obtained from the hyphae of shiitake was turned into a white emulsion by adding hydrochloric acid, that the extract had the effect of suppressing cancer and that the fruiting body of shiitake extended its height and cap dimension to surprising extents overnight. As a result of analysis of that liquid extract, organic germanium was found to be present in that liquid. It was thought that the germanium was present not as such, i.e., not in the form of the element, but in the form of complex salts with polysaccharides in the metabolic liquids in the hyphal cells.

The present invention is predicated on the foregoing findings, and it seeks to provide novel uses of the organic germanium component in the hyphae of edible fungi.

SUMMARY OF THE INVENTION

The primary object of the invention is to accelerate or promote the growth of plants with the organic germanium component in the hyphae of edible fungi.

Another object of the invention is to greatly increase the yield of crops, particularly of the soybean and like crop plants, by means of the aforementioned organic germanium component.

A further object of the invention is to provide a substance useful for the growth of plants at a low cost.

DESCRIPTION OF THE PREFERRED EMBODIMENTS

The fungi that may be employed in accordance with the invention include shiitake, nameko and enokidake, but the most effective is shiitake. There are various ways that are employed for culturing seed fungi. According to the invention, pieces of the mycelium cut from the fruiting body of an edible fungus such as shiitake are cultured in an agar nutrient medium. The seed structure produced in this way is then transferred to a so-called GPY bed (a liquid nutrient medium consisting of a mixture of glucose, peptone and yeasts for shaking culture). Thereafter, the hyphae are taken out of the GPY bed by means of an injector needle and planted in a solid nutrient medium.

The solid nutrient medium may be a sawdust nutrient medium (prepared by mixing sawdust and rice bran in a ratio of 3 to 1), which has heretofore been used for the culture of shiitake and like fungi. Alternatively, it is possible to use a bagasse nutrient medium developed earlier by the inventors and consisting of bagasse (with bagasse and rice bran in a ratio of 3 to 1) or a beet remains nutrient medium consisting of remains of sugar beet (with beet remains and rice bran in a ratio of 12 to 1). In case of the sawdust nutrient medium, the growth of the plant is liable to be adversely affected by harmful components such as resin acid contained in the sawdust which is the main material of the medium. For this reason, it is preferred to use the bagasse or beet remains nutrient medium, and in fact better growth and yield could be obtained with these media.

In addition, in case of the bagasse or beet remains nutrient medium very good results are obtainable even by reusing the waste nutrient medium that is left after harvesting the fruiting bodies. In particular, bagasse finds no customary use and is usually burnt up, so it is easily and inexpensively available. If sawdust is used for the nutrient medium, it is preferably refined in advance. In one method of refinement, the sawdust is immersed in a 1-% sal soda solution for 24 hours to drive out the harmful components such as resin acid through dissolution, followed by washing with water 4 to 5 times and removal of the water content.

The nutrient medium is sterilized before the cultured seed structure or "spawn" is planted. After planting, the medium is placed in a culture chamber to start the culture of the hyphae. If possible, the nutrient medium is then moved to an air-conditioned chamber capable of temperature adjustment for subjecting to a desired temperature change treatment. After the medium has become prevalent with hyphae and immediately before the bursting of sporophores or fruiting bodies, the medium is crushed into pieces, which are then heated together with added water to accelerate the self-digestion of the hyphae to obtain a suspension containing the intended useful substance. The extraction of the useful substance may be done by any means. According to the invention, the suspension is charged into a filter sac made of funnel cloth to squeeze out the liquid, which is then dialyzed with a membrane filter.

The liquid extract obtained in this way is then dissolved in water to form a 300 to 500 times diluted liquid, which is sprayed over the leaves of plants or mixed with the soil for the desired effects.

The extract obtained according to the invention is found to be very effective for the cultivation of such crop plants as soybean, French bean, eggplant, tomato, cucumber and turnip. Particularly, it can surprisingly increase the yield of the soybean crop up to 2.6 times. Also, by immersing the seedling of tobacco in a 500 times diluted liquid of the extract before planting and by spraying the liquid over the leaves of this plant, very flourishing growth, particularly of the root, and quite satisfactory color of leaves could be obtained. In particular, good results could be obtained in keeping the tobacco mosaic disease in check. Further, the disease caused by *Plasmopara viticola* (Berkley et Curtis) Berlese et de Toni of prince melon could be perfectly cured by spraying a 300 times diluted liquid of the extract twice over the leaves of this affected plant, and the yield thereof was almost equal to that of the normal plant of the same species.

Some examples of the invention are given in the following.

EXAMPLE I

A nutrient medium composed of 60% of bagasse, 20% of rice bran and 20% of other nutrient sources such as wheat bran was sterilized in the usual way, and the aforementioned cultured seed structure of shiitake was planted in the sterilized medium. The medium was then placed in an air-conditioned culture chamber at a temperature of 18° to 20°C and a relative humidity of 60% to start the culture of the hyphae. When it became sufficiently prevalent with hyphae, it was moved to a temperature treatment chamber for temperature treatments. Here, it was first held at a high temperature (33° to 34°C) for a period of 24 to 48 hours, and then it was subjected to a low temperature treatment at temperatures ranging from 5° to 8°C and a relative humidity of 85% for 5 to 7 days. Thereafter, it was moved to a growth chamber held at a temperature of 10° to 16°C and a relative humidity of 90% and left there for about 10 days. Around the end of this period, sporophores began to burst through the surface of the nutrient medium. At this instant, the medium was taken out and crushed by means of a crusher into pieces or particles as large as the thumb tip. Then, to 1,000 grams of these particles was added 5 liters of sterilized water, and the pH was adjusted to 4.5 to 5.0. The system thus formed was then sealed in a plastic vessel for heating at 45° to 50°C for 4 to 5 hours, thereby favorably promoting the self-digestion of the hyphae with $\beta$-1-3 glucanase and chitinase resulting from the hyphal metabolism. The resultant system in the form of a suspension was then charged into a filter sac of funnel cloth for filtering under pressure, and the fltrate was then dialyzed with a membrane to obtain a liquid extract containing the useful hyphal derivatives of shiitake. As a result of analysis of this extract, 60 ppm of organic germanium was found to be contained (the analysis being conducted by Japan Foodstuff Analysis Center, a juridical foundation).

In order to confirm that the above liquid extract was effective for bettering the growth and yield of the soybean, the following experiments were undertaken.

EXPERIMENT I

Site: A hothouse of Noda Shokkukin Kogyo Inc., Noda City, Chiba
Period: February through May, 1974
Directed by: Hiroaki Maeda
Procedure:

1. Cultivation

A variety called "miho shiratori edamame (green soybean)" was selected. The seeding was done on Feb. 26, and the planting was done on Mar. 29. The cultivation was carried out hydroponically (using 10-liter pots). The hothouse temperature was adjusted to range from 10° to 25°C. The hydroponic liquid used contained 42.3 ppm of nitrogen, 40 ppm of phosphorus, 55 ppm of potassium, 9.7 ppm of magnesium, 8 ppm of calcium, 13.5 ppm of iron, 0.5 ppm of boron, 0.02 ppm of copper, 0.5 ppm of manganese, 0.05 ppm of molybdenum and 0.05 ppm of zinc, and it was used throughout the culture period.

2. Use of the extract

The culture pots were divided into three groups each of five pots. For group A, no extract was given; the plant was grown with the hydroponic liquid alone. For group B, a 500 times diluted liquid of the extract was added to the hydroponic liquid. For the remaining group C, a 1,000 times diluted liquid of the extract was added to the hydroponic liquid.

3. Examination

Height of the plant in growth, number of pods per pot of the plant in growth and net weight of root portion, stalk and leaf portion and seed portion (inclusive of the pod) of the plant at the time of harvest were measured, and the results are listed in the following tables.

Table 1

| | | Height in growth (of centimeters) | | | |
|---|---|---|---|---|---|
| | | Seeding March | 4/9 | 4/15 | 4/25 |
| Group A | 1 | 11 | 20 | 27 | 46 |
| | 2 | 10 | 17 | 25 | 40 |
| | 3 | 12 | 20 | 28 | 50 |
| | 4 | 12 | 21 | 30 | 50 |
| | 5 | 7 | 15 | 20 | 33 |
| | Average | 10.4 | 16.6 | 26.0 | 43.8 |
| Group B | 6 | 12 | 25 | 37 | 60 |
| | 7 | 10 | 21 | 31 | 52 |
| | 8 | 11 | 22 | 32 | 60 |
| | 9 | 10 | 25 | 34 | 61 |
| | 10 | 7 | 15 | 22 | 45 |
| | Average | 10.0 | 22 | 32 | 55.6 |
| Group C | 11 | 12 | 28 | 40 | 71 |
| | 12 | 11 | 25 | 39 | 70 |
| | 13 | 12 | 28 | 40 | 60 |
| | 14 | 10 | 20 | 30 | 63 |
| | 15 | 7 | 18 | 26 | 42 |
| | Average | 10.4 | 23.8 | 35 | 61.5 |

Table 2

| | | Number of pods | | |
|---|---|---|---|---|
| | | 5/11 | 5/14 | 5/17 |
| Group A | 1 | 15 | 15 | 15 |
| | 2 | 11 | 12 | 12 |
| | 3 | 14 | 13 | 18 |
| | 4 | 16 | 22 | 22 |
| | 5 | 6 | 10 | 11 |
| | Average | 12.4 | 15.4 | 15.6 |
| Group B | 6 | 20 | 21 | 21 |
| | 7 | 15 | 16 | 18 |
| | 8 | 17 | 22 | 22 |
| | 9 | 15 | 19 | 20 |
| | 10 | 17 | 19 | 23 |
| | Average | 16.8 | 19.2 | 20.8 |
| Group C | 11 | 18 | 20 | 21 |
| | 12 | 21 | 23 | 25 |
| | 13 | 14 | 15 | 15 |
| | 14 | 12 | 13 | 13 |
| | 15 | 6 | 13 | 15 |
| | Average | 14.2 | 16.8 | 17.8 |

Table 3

| | | Net weight at the time of harvest (in grams) | | |
|---|---|---|---|---|
| | | Root portion | Stalk and portion leaf | Seed portion (inclusive of the pod) |
| Group A | Total | 205 | 140 | 135 |
| | Average | 41 | 28 | 27 |
| Group B | Total | 235 | 210 | 200 |
| | Average | 47 | 42 | 40 |
| Group C | Total | 225 | 145 | 155 |
| | Average | 45 | 29 | 31 |

As is seen from the above tables, group C is the highest in height growth. At the time of harvest, however, there was no substantial difference of height between groups C and A. In the weight of various portions, group B surpassed group A by 50 percent at the time of harvest. In the weight of the seed portion, groups B and C surpassed group A respectively by 50 percent and 20 percent, and thus the most pronounced effects were observed in group B.

In the water culture, it is quite difficult to observe the influence of nodule bacteria characteristic to the plants which belong to Leguminosae, so it is necessary to test the reproducibility in soil culture. Accordingly, the inventors undertook the following experiment.

EXPERIMENT II

Site: A field owned by Endo in Noda City, Chiba
Period: March through June, 1974
Procedure:

1. Cultivation

"Okuhara" (a variety of very early ripening) was selected. The seeding was done on Mar. 15, and the planting was done on Apr. 15. The cultivation was carried out on exposed soil. As manure, 15 kilograms of a chemical fertilizer (N12 P12 K12), 800 kilograms of heap manure and 1 ton of droppings of fowls were supplied per 10 acres in advance.

2. Use of the extract

The field was divided into three sections. In section A, no extract was given; the plant was grown with the manure alone. In section B, a 500 times diluted liquid of the extract was sprayed over the leaves three times after the manuring, that is, on May 4 (before the flowering time), May 18 (after the flowering time) and May 28 (fructifying time). In the remaining section C, the 500 times diluted liquid was sprayed twice after the manuring, that is, on May 18 and May 28.

3. Examination

The following tables list the number of pods per sample plant and net weight of various portions of the plant, measured for 20 sample plants for each section.

TABLE 4

Number of pods per sample plant measured on June 4

Section A: 10, 2, 2, 2, 5, 7, 7, 11, 10, 4, 9, 6, 7, 6, 6, 6, 7, 3, 3, 10,
Total: 123
Average: 6.2

Section B: 15, 16, 15, 4, 17, 8, 10, 16, 15, 10, 8, 20, 16, 16, 16, 14, 12, 13, 13, 12,
Total: 266
Average: 13.3

Section C: 11, 6, 3, 18, 14, 7, 14, 10, 6, 8, 11, 6, 8, 12, 8, 11, 12, 9, 7,
Total: 188
Average: 9.4

As is seen, the numbers in sections B and C are respectively 2.16 and 1.53 times that in section A.

Table 5

|  |  | Net weight at the time of harvest (in grams) | | |
|---|---|---|---|---|
|  |  | Root portion | Stalk and leaf portion | Seed portion (inclusive of the pod) |
| Section A | Total | 146 | 100 | 167 |
|  | Average | 29 | 20 | 33 |
| Section B | Total | 275 | 250 | 435 |
|  | Average | 55 | 50 | 87 |
| Section C | Total | 264 | 173 | 334 |
|  | Average | 53 | 35 | 67 |

Note:
The harvesting was made on June 25 in section A, on June 18 in section B and on June 25 in Section C.

As is seen, in sections B and C the net weight is respectively 2.6 and 2 times that in section A.

It will be seen from the above tables that the yield in section B is surprisingly 2.6 times that in section A. The 500 times diluted liquid was found to be most effective.

The harvest in section B (three times treated area) was made 1 week earlier than section A (no treatment area) and section C (twice treated area).

EXAMPLE II

A sawdust nutrient medium composed of 60% of sawdust, 20% of rice bran and 20% of other nutrient sources such as wheat bran was sterilized in the usual way, and the cultured seed structure of shiitake was planted in the sterilized medium. Thereafter, the fungus was cultured in the same way as in the previous Example I until it became prevalent with hyphae. Subsequently, right before the bursting of sporophores the medium was crushed into particles as large as the thumb tip, which were then heated together with added water in the same way as in Example I to obtain a suspension, which was similarly filtered to obtain a liquid extract.

In order to see what effect this extract had on the cultivation of turnip, the following experiment was undertaken.

EXPERIMENT III

Site: A field of Noda Shokkin Kogyo Inc., Noda City, Chiba
Period: May through June, 1974
Directed by: Hiroaki Maeda
Procedure:

1. Cultivation

A variety called "anti-disease hikari-kabu" was selected. The seeding was done on May 1, and the harvest was made on June 13. The cultivation was carried out on the exposed soil. As manure, 50 kilograms of a chemical fertilizer (N16 P16 K16) was supplied per 10 acres in advance.

2. Use of the extract

The culture field was divided into two sections. In section A, no extract was given; the plant was grown with the manure alone. In the other section B, a 300 times diluted liquid of the extract was sprayed over the leaves twice after the manuring, that is, on May 11 when the plant had two leaves and on May 25 when the root began to grow plump.

3. Examination

The following table shows the net weight of the leaf portion and root portion of the plant at the time of harvest, the measurement being made on 10 samples for each section.

Table 6

|  | Net weight at the time of harvest (in grams) | | | | | | | | | | |
|---|---|---|---|---|---|---|---|---|---|---|---|
|  | 1 | 2 | 3 | 4 | 5 | 6 | 7 | 8 | 9 | 10 | Average |
| Section B |  |  |  |  |  |  |  |  |  |  |  |
| Leaf portion | 65 | 70 | 65 | 55 | 77 | 60 | 70 | 77 | 75 | 75 | 69 |
| Root portion | 80 | 70 | 70 | 57 | 98 | 48 | 70 | 70 | 60 | 47 | 67 |
| Section A |  |  |  |  |  |  |  |  |  |  |  |
| Leaf portion | 55 | 50 | 53 | 45 | 35 | 40 | 40 | 30 | 25 | 55 | 43 |
| Root portion | 35 | 35 | 45 | 32 | 30 | 30 | 27 | 34 | 20 | 35 | 32 |

As is seen, in section A the leaf portion and the root portion respectively weighed 160 percent and 208 percent with respect to those in section B.

Regarding the height, a difference of about 3 centimeters was recognized a week after replanting made when the plant had eight leaves. Also, at this time there was a great difference in the size of the root. In the stage of nutritive growth, the height again differed by about 3 centimeters. Also, section B was richer in chlorophyll and again there was a difference in the size of the root. On June 13, the plant in section B was in its initial stage of flowering, but the plant in section A still had no flower bud. At this time, it was thought that there was a difference of about 5 days in growth, and there was a height difference of about 8 centimeters.

EXAMPLE III

In order to see what effect the liquid extract of the shiitake obtained in Example I had upon the cultivation of tobacco, the following experiment was undertaken.

EXPERIMENT IV

Site: Asahi-mura, Kashima-gun, Ibaraki Prefecture
Period: April through June, 1974
Directed by: Hiroaki Maeda
Procedure:
1. Cultivation The planting was made from Apr. 10 through Apr. 18. The exposed soil culture was adopted.

2. Use of the extract

The test area was divided into two sections. In section A (2020 plants being planted per 10 acres) no extract was given; the plant was grown with chemical fertilizer and heap manure alone. In the other section B (2020 plants being planted per 10 acres), a 400 times diluted solution of the extract was sprayed over the leaves after the supply of chemical fertilizer and heap manure. More particularly, the seedling for this section was immersed in the 400 times diluted solution before the planting, and the spraying was made four times at an interval of 14 days during the growth period.

3. Examination

Examination of the state of taking root of the planted seedlings and state of growth of the plant and checking for diseases were made in eight test fields.

Checking of the tobacco mosaic disease was made a week after replanting when the plant had eight leaves, and the results are shown in the following table.

Table 7

| | Tobacco mosaic disease (number of attacked plants per 10 acres, that is, 2020 plants) | |
|---|---|---|
| | Section B (treated with the extract) | Section A (not treated) |
| Field A | 4 | 20 |
| B | 3 | 6 |
| C | 0 | 2 |
| D | 400 | 1400* |
| E | 10 | 25 |
| F | 6 | 6** |
| G | 0 | 3 |

Table 7-continued

| Tobacco mosaic disease (number of attacked plants per 10 acres, that is, 2020 plants) | |
|---|---|
| Section B (treated with the extract) | Section A (not treated) |
| H  0 | 2 |

*In the field A the mosaic disease is seriously caused every year, and in the last year it attacked about 70 percent of the plants (1400 plants).
**In the field B the seedling to be planted was not immersed in the extract solution.

Examination of the height, which was also made a week after the replanting, revealed a difference of about 3 centimeters between the two sections B and A. Also, at this time the size of the root differed greatly (being greater in section B).

In the stage of nutritive growth, the height again differed by about 3 centimeters. Also, section B was richer in chlorophyll, and again there was a difference in the size of the root.

On June 10, the plant in section B was on its initial stage of flowering, but the plant in section A still had no flower bud. At this time, there was thought to be a difference of about 5 days in growth, and there was a difference of about 8 centimeters in height.

In conclusion, the above experiment showed that section B was superior in taking root and growing of the plant. Also, the extract according to the invention seemed to have an effect of holding the tobacco mosaic disease in check.

Although the tobacco mosaic disease are seen the most during the growth period of tobacco leaves, in these experiments above very little was seen during this growth period, that is, the data obtained from these experiments is regarded as not to be fluctuating in the future.

We claim:

1. A method of promoting the growth of a plant whose growth is promoted by germanium, comprising applying to the leaves of said plant or to the soil surrounding said plant a growth promoting amount of an organic germanium component obtained by extracting the hyphae of an edible fungus selected from the group consisting of shiitake, nameko and enokidake in combination with a liquid carrier.

2. The method of claim 1 wherein the liquid carrier is water.

3. The method of claim 1 wherein the fungus is shiitake.

4. The method of claim 3 wherein the liquid carrier is water.

5. The method of claim 1 wherein the plant is selected from the group consisting of soybean, French bean, eggplant, tomato, cucumber, turnip and tobacco plants.

6. The method of claim 5 wherein the fungus is shiitake.

7. The method of claim 6 wherein the liquid carrier is water.

8. The method of claim 7 wherein the plant is soybean.

9. The method of claim 7 wherein the plant is tobacco.

* * * * *